United States Patent
Marszalek

(10) Patent No.: US 6,268,737 B1
(45) Date of Patent: Jul. 31, 2001

(54) METHOD AND SYSTEM FOR DETERMINING OIL QUALITY

(75) Inventor: Gary A. Marszalek, South Lyon, MI (US)

(73) Assignee: Detroit Diesel Corporation, Detroit, MI (US)

( * ) Notice: Subject to any disclaimer, the term of this patent is extended or adjusted under 35 U.S.C. 154(b) by 0 days.

(21) Appl. No.: 09/413,921

(22) Filed: Oct. 7, 1999

(51) Int. Cl.[7] .......................... G01R 27/26; G01R 27/08; G06F 19/00
(52) U.S. Cl. .......................... 324/663; 324/667; 324/658; 324/690; 324/698; 702/13; 702/25
(58) Field of Search .................... 324/663, 667, 324/658, 674, 681, 690, 698; 702/13, 25

(56) References Cited

U.S. PATENT DOCUMENTS

| | | |
|---|---|---|
| 3,753,092 | 8/1973 | Ludlow et al. . |
| 3,774,238 | 11/1973 | Hardway, Jr. . |
| 4,058,766 * | 11/1977 | Vogel et al. .......................... 324/667 |
| 4,258,422 | 3/1981 | Dougherty et al. . |
| 4,322,678 * | 3/1982 | Capots et al. .......................... 324/663 |
| 4,646,070 * | 2/1987 | Yasuhara et al. ...................... 340/603 |
| 4,857,829 | 8/1989 | Sagae et al. . |
| 4,924,702 | 5/1990 | Park . |
| 5,262,732 * | 11/1993 | Dickert et al. ........................ 324/672 |
| 5,274,335 | 12/1993 | Wang et al. . |
| 5,540,086 | 7/1996 | Park et al. . |
| 5,604,441 | 2/1997 | Freese et al. . |
| 5,900,810 | 5/1999 | Park et al. . |
| 5,907,278 | 5/1999 | Park et al. . |
| 5,929,754 * | 7/1999 | Park et al. ............................ 340/439 |
| 5,973,503 | 10/1999 | Kuipers et al. . |

* cited by examiner

*Primary Examiner*—Safet Metjahic
*Assistant Examiner*—Anjan K Deb
(74) *Attorney, Agent, or Firm*—Brooks & Kushman P.C.

(57) ABSTRACT

A method for determining quality of lubricating oil includes positioning first and second electrodes in the oil, wherein the electrodes are coated with an electrically insulating material; applying a symmetrically balanced time-varying potential to the electrodes, the potential having a predetermined amplitude; sweeping the potential over a range of frequencies from a first frequency to a second frequency greater than the first frequency; monitoring magnitude of amplitude modulation of the potential over the range of frequencies; and determining the quality of the oil based on variation of the amplitude modulation. A system for practicing the method is also provided.

13 Claims, 3 Drawing Sheets

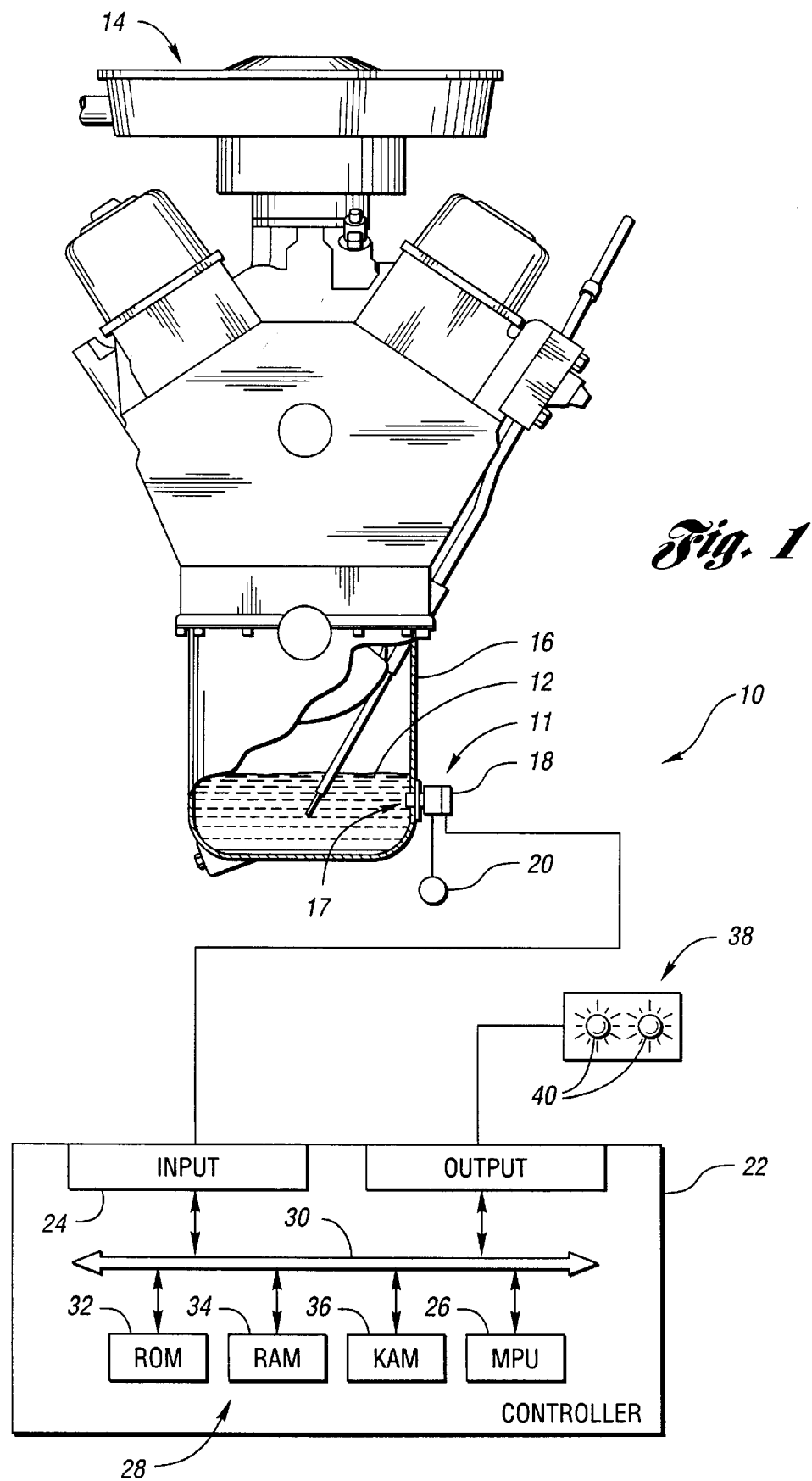

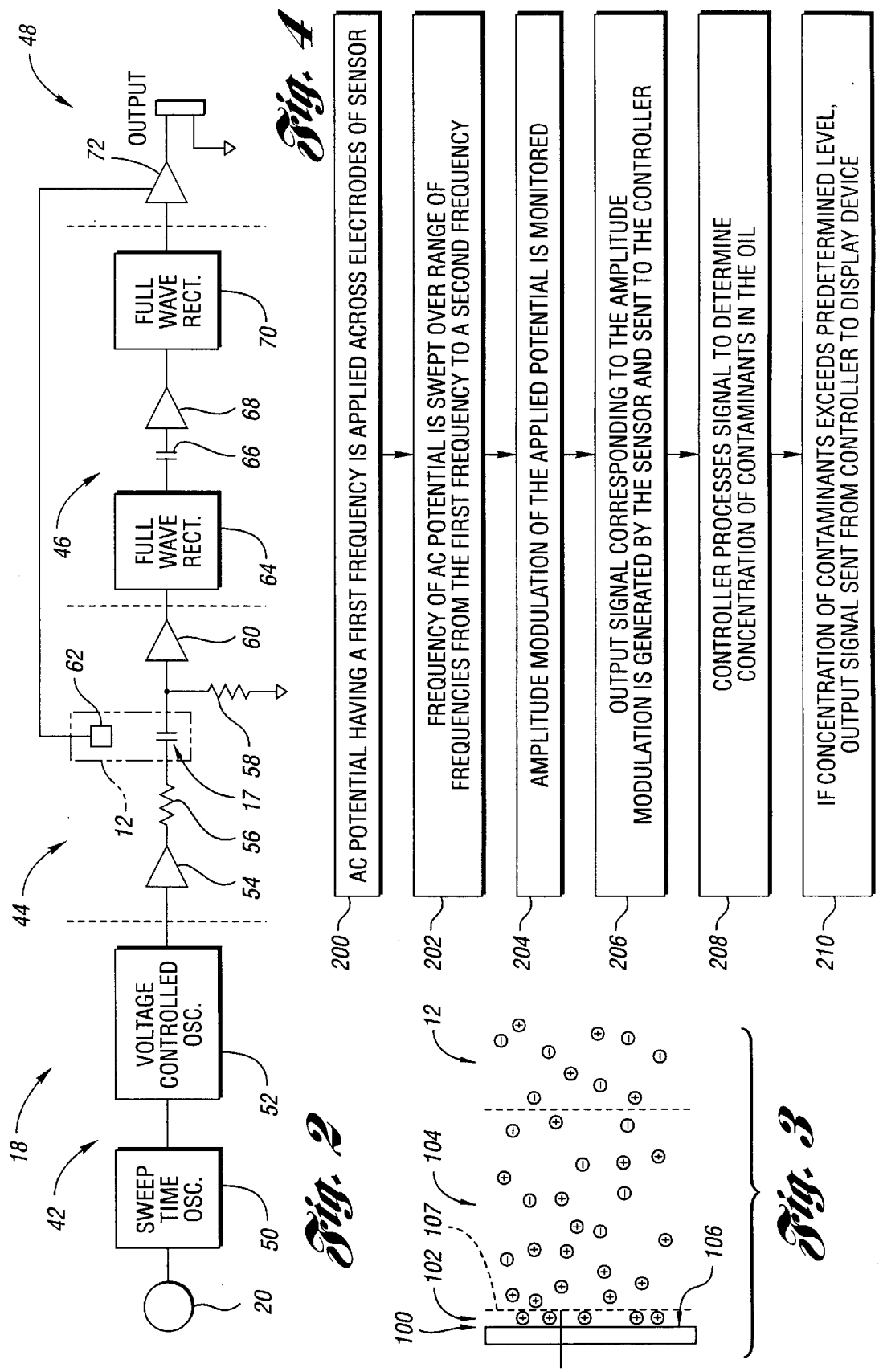

METHOD AND SYSTEM FOR DETERMINING OIL QUALITY

TECHNICAL FIELD

The invention relates to a method and system for accurately determining oil quality, wherein the method and system involve applying a potential across two electrodes disposed in the oil, and varying frequency of the potential over a range of frequencies.

BACKGROUND ART

Lubricating oil improves the efficiency and durability of such systems as internal combustion engines, compressors, pumps and gear boxes. The presence of contaminants in the oil, however, significantly affects the performance of the oil. Such contaminants include soot, dissolved gases, dissolved liquids, emulsified liquids, and particles resulting from system wear.

Many methods and systems have been developed to detect contaminants in oil. One prior system, for example, includes a capacitive oil deterioration sensor that is used to determine the dielectric constant of engine oil based on the capacitive reactance of the oil. The theory behind this sensor is that the dielectric constant of the oil is related to the concentration of contaminants in the oil. Assuming the oil is a perfect insulator, the capacitive reactance $X_c$ of the oil can be expressed as:

$X_c=1/(2\pi fC)$, where f is the frequency of a potential applied across the sensor, and C is the capacitance of the oil.

While the capacitive reactance can be measured with little error in non-polar oil, measurement error increases with increasing conductivity of the oil due to solution current flowing through the oil.

Generally, newly refined base oil stock is a non-polar solution. When it is formulated for lubricating oil, various additives are added to improve performance and extend the useful life of the oil. Many of these additives, however, are polar and increase the conductivity of the oil. Conductivity of the oil further increases with increasing temperature. Even as "new" oil reaches operating temperatures, minor solution current can be detected. Solution current also increases as contaminants increase in the oil during use.

Furthermore, prior art methods and systems typically utilize an unbalanced alternating current (AC) or static direct current (DC) potential that causes migration of polar contaminants toward oppositely charged sensor electrodes. Eventually, this contaminant migration results in build up of contaminants on the electrodes, which contributes to erroneous capacitive reactance measurements of the oil. A prior approach to reduce contaminant buildup has been to coat one or both of the electrodes with a non-stick surface such as TEFLON®. This approach, however, does not reduce polar contaminant migration toward the electrodes.

DISCLOSURE OF INVENTION

The invention overcomes the shortcomings of the prior art by providing a new and improved method for determining oil quality that involves varying frequency of a potential applied to electrodes immersed in the oil, in order to evaluate error capacitance resulting from contaminants in the oil.

Under the invention, a method for determining quality of lubricating oil using first and second electrodes in contact with the oil includes applying a timevarying potential to the electrodes; varying frequency of the potential over a range of frequencies from a first frequency to a second frequency greater than the first frequency; monitoring magnitude of amplitude modulation of the potential over the range of frequencies; and determining the quality of the oil based on variation of the amplitude modulation.

Advantageously, because error capacitance is frequency dependent, the effects of error capacitance can be determined by varying the frequency of the applied potential. Furthermore, because error capacitance is related to the concentration of contaminants in the oil, oil quality can be quickly determined by evaluating error capacitance.

Preferably, the method also includes electrically insulating at least one of the electrodes from the oil to inhibit current from passing from the electrode through the oil. Furthermore, the applied potential is preferably symmetrically balanced so as to minimize contaminant buildup on one or both of the electrodes.

Further under the invention, a method for determining quality of lubricating oil using electrodes in contact with the oil includes determining error capacitance resulting from contaminants in the oil; and determining the quality of the oil based on the error capacitance.

A system according to the invention for determining quality of lubricating oil includes first and second electrodes adapted to contact the oil. The system further includes a microprocessor in communication with the electrodes. The microprocessor includes instructions for applying a time-varying potential to the electrodes; instructions for varying frequency of the potential over a range of frequencies from a first frequency to a second frequency greater than the first frequency; instructions for determining amplitude modulation of the potential over the range of frequencies; and instructions for determining the quality of the oil based on the amplitude modulation.

These and other objects, features and advantages of the invention are readily apparent from the following detailed description of the best modes for carrying out the invention when taken in conjunction with the accompanying drawings.

BRIEF DESCRIPTION OF DRAWINGS

FIG. 1 is a schematic diagram of a system for determining oil quality according to the invention including a sensor mounted to an oil reservoir of a motor vehicle engine and having a control circuit;

FIG. 2 is an exemplary embodiment of the control circuit;

FIG. 3 is a schematic diagram of a sensor electrode immersed in oil, and showing an electrical double-layer formed at the interface of the electrode and the oil;

FIG. 4 is a flow chart illustrating operation of a system or method according to the invention for determining oil quality based on electrical double-layer effects;

BEST MODES FOR CARRYING OUT THE INVENTION

Figure 5:
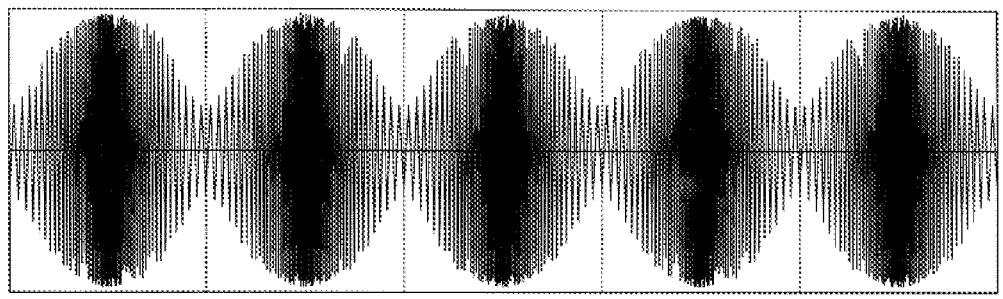
FIG. 5 is a graph showing an exemplary response of relatively clean oil.

FIG. 1 shows a system 10 according to the invention for determining quality of lubricating oil 12 in a motor vehicle engine 14, or other suitable arrangement such as a compressor, pump or gear box. The system 10 includes a sensor 11 adapted to be mounted to an oil reservoir 16 of the engine 14. The sensor 11 has two spaced electrodes 17 adapted to be immersed in the oil 12, and a control circuit 18. When the electrodes 17 are joined by the oil 12, which is generally a dielectric material, a capacitor is formed.

As further shown in FIG. 1, the sensor 11 is connected to a power source 20. The power source 20, in combination with the control circuit 18, is used to apply a time-varying potential, such as an AC potential, across the electrodes 17. The power source 20 may, for example, include a motor vehicle battery and a DC to DC converter for providing regulated positive and negative voltages to the control circuit 18. Preferably, the power source 20 and the control circuit 18 cooperate to provide a substantially symmetrically balanced sinusoidal AC potential across the electrodes 17, as explained below in greater detail, such that substantially no DC bias is created across the electrodes 17. Such a potential reduces or eliminates contaminant build up on the electrodes 17 as explained below in greater detail. Alternatively, the power source 20 and control circuit 18 may provide any suitable time-varying potential, such as a triangular or square waveform potential, such that substantially no DC bias is created across the electrodes 17.

The system 10 further includes a controller 22 in electrical communication with the sensor 11 via input ports 24 of the controller 22. The controller 22 preferably includes a microprocessor 26 in communication with various computer readable storage media 28 via data and control bus 30. The computer readable storage media 28 may include any of a number of known devices which function as a read-only memory (ROM) 32, random access memory (RAM) 34, keep-alive memory (KAM) 36, and the like. The computer readable storage media 28 may include data representing program instructions (software), calibrations, operating variables and the like that are used in conjunction with associated hardware to effect control of the system 10. The computer readable storage media 28 may be implemented by any of a number of known physical devices capable of storing data representing instructions executable via a computer such as controller 22. Known devices may include, but are not limited to, PROM, EPROM, EEPROM, flash memory, and the like in addition to magnetic, optical, and combination media capable of temporary or permanent data storage.

In operation, the controller 22 receives signals from the sensor 11 via input ports 24, and generates output signals that may be provided to various ctuators and/or components, such as a display device 38, which may include various indicators such as lights 40 to communicate information relative to oil quality to the operator of the vehicle. Of course, alphanumeric, audio, video, or other displays or indicators may be utilized if desired. In a preferred embodiment, the controller 22 is a Detroit Diesel Electronic Controller (DDEC) available from Detroit Diesel Corporation, Detroit, Michigan.

While many control circuits having various hardware and software components can be utilized with the system 10, a simplified schematic representation of an exemplary embodiment of the control circuit 18 is shown in FIG. 2. The control circuit 18 includes a frequency oscillating portion 42, a drive balancing portion 44, a demodulation and filtering portion 46, and a scaling portion 48.

The frequency oscillating portion 42 is connected to the power source 20, and is used to vary the frequency of the potential provided by the power source 20. The frequency oscillating portion 42 includes a sweep time oscillator 50 for establishing a frequency sweep time span, and a voltage controlled oscillator 52 for varying frequency of the applied potential.

The drive balancing portion 44 is used to symmetrically balance the applied potential across the electrodes 17 of the sensor 11 such that substantially no DC bias exists between the electrodes 17. The drive balancing portion 44 includes a first operational amplifier 54 and a balancing resistor 56 connected to one of the electrodes 17, and a load resistor 58 and a second operational amplifier 60 connected to the opposite electrode 17. These components are preferably selected such that the impedance of the first amplifier 54 and the balancing resistor 56 is equal to the impedance of the load resistor 58 and the second amplifier 60.

A temperature sensor 62 is also disposed proximate the electrodes 17 for sensing temperature of the oil 12. The temperature sensor 62 provides a temperature output signal to the scaling portion 48, which adjusts output from the sensor 11 as explained below in greater detail.

The demodulation and filtering portion 46 includes a first precision full wave active rectifier 64 for accurately rectifying output from the drive balancing portion 44 to provide a signal that has a DC component, which represents the applied potential, and a superimposed AC component. The signal from the first rectifier 64 is then passed through a first capacitor 66, which blocks the DC component of the signal, and a third operational amplifier or band pass filter 68 for filtering the signal and demodulating the signal. The demodulated signal is then passed through a second precision full wave active rectifier 70 for accurately converting the demodulated signal to a DC signal.

The scaling portion 48 includes a fourth operational amplifier 72 for adjusting scaling voltages indicative of clean and contaminated oil. The scaling portion 48 also receives the temperature output signal from the temperature sensor 62, and adjusts the DC signal as necessary to compensate for temperature of the oil 12. The scaling portion 48 then provides an output signal to the controller 22, which processes the signal as described below in greater detail. Alternatively, the temperature sensor 62 may provide the temperature output signal directly to the controller 22, which may adjust the output signal provided by the scaling portion 48 to compensate for temperature of the oil 12.

Although the electrodes 17 form a capacitor when immersed in the oil 12, the sensor 11 may exhibit some form of leakage current or solution current due to polar additives and/or contaminants in the oil 12. The additives and/or contaminants carry charge through the oil 12 from one electrode to another, thereby creating the solution current. There is a minimum voltage requirement, however, that must be exceeded before charge will transfer from one of the electrodes 17 to the additives and/or contaminants in the oil 12 such that the solution current will flow. This minimum voltage requirement, known as the redox potential, varies with the concentration of additives and/or contaminants in the oil 12.

Prior art sensors that attempt to measure capacitive reactance of oil fail to adequately account for solution current. Solution current, which can be schematically modeled as a variable resistance in parallel with a particular sensor, results in the sensor measuring total impedance of the oil and not just the capacitive reactance of the oil. Capacitive reactance $X_c$ can be expressed as:

$X_c = 1/(2\pi f C)$, where f is the frequency of a potential applied across the sensor, and C is the capacitance of the oil.

Total impedance Z, for an oil resistance R and a capacitive reactance $X_c$ in parallel, can be expressed as:

$$Z = R X_c / \sqrt{(R^2 + X_c^2)}$$

Comparing the above equations at various oil resistance values reveals how solution current can dramatically affect measured results of such prior art sensors.

Prior art sensors also fail to account for the effects of contaminant buildup or adsorption on the electrodes 17, which contributes to the formation of an electrical double-layer at the electrode/oil interface 100 at each of the electrodes 17, as shown in FIG. 3. Each electrical double-layer comprises first and second or inner and outer distinct layers 102 and 104, respectively, of equal charge density. The inner layer 102, known as the Stern layer, is in direct contact with a surface 106 of a particular electrode and extends to the shear plane or Outer Helmholtz Plane (OHP) 107. The electrical potential decay within the inner layer 102 is roughly linear. The outer layer 104, known as the diffuse layer, extends from the OHP into the oil 12. Electrical potential decays exponentially in the outer layer 104, and the thickness of the outer layer 104 depends on contaminant concentration and other parameters. Furthermore, the outer layer 104 is characterized by the Debye-Huckel contstant (k), which defines the exponential decay of the electrical potential away from OHP into the oil 12.

At the electrode/oil interface 100 of each of the electrodes 17, both faradaic and non-faradaic processes may occur. Faradaic processes involve actual electron transfers between the electrodes and the oil 12. An example of a faradaic process is solution current, which is described above in detail. During non-faradaic processes, no charge actually crosses the electrode/oil interface. However, electrode transient currents flow to charge or discharge the electrical double-layers as the polarity of an applied potential changes. This charging and discharging of the electrical double-layers is perceived as error capacitance, which is a direct function of the thickness of the electrical double-layers.

The electrical double-layers and resulting error capacitance also vary with amplitude of the applied potential, frequency of the applied potential, oil temperature, oil viscosity, contaminant size and contaminant concentration. Generally, error capacitance resulting from the electrical double-layers will increase with increasing contaminant concentrations. Furthermore, error capacitance decreases with increasing frequency of the applied potential.

FIG. 4 illustrates operation of a method or system, such as the system 10, for determining oil quality based on electrical double-layer effects. At step 200, an AC potential having a first amplitude and a first frequency is applied across the electrodes 17 of the sensor 11 using the power source 20 and control circuit 18. At step 202, the the frequency of the AC potential is swept over a range of frequencies from the first frequency to a second frequency greater than the first frequency, while maintaining the amplitude of the AC potential at the first amplitude. While the frequency may be swept over any suitable range and over any suitable frequency sweep time span depending on such parameters as amplitude of the applied potential, oil temperature, and contaminant size, frequency is preferably swept from 10 kilohertz (KHz) to 100 KHz over a frequency sweep time span of 0.001 seconds.

Figure 6:
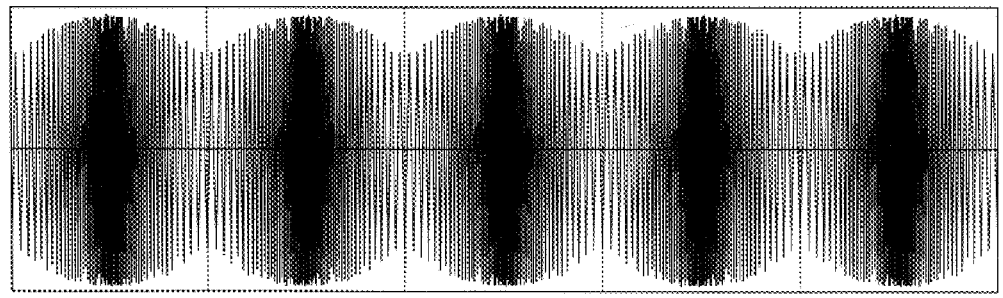
FIG. 6 is a graph showing an exemplary response of relatively contaminated oil.

At step 204, which occurs as the frequency is being swept over the range of frequencies, amplitude variation of the applied potential, or amplitude modulation, resulting from the electrodes 17 and the oil 12 is continuously monitored or otherwise determined. This step, for example, may be represented as the output from the drive balancing portion 44 of the control circuit 18. Furthermore, the amplitude modulation is directly dependent on error capacitance resulting from the electrical double-layers. Because voltage output of an ideal capacitor increases with increasing frequency, amplitude of the applied potential is at a minimum when the frequency is at 10 KHz, and amplitude of the applied potential is at a maximum when the frequency is at 100 KHz. FIGS. 5 and 6 show exemplary amplitude modulations for a relatively clean oil and for a relatively contaminated oil, respectively. As shown in FIGS. 5 and 6, the difference between the maximum and minimum amplitudes is greater for the clean oil. In other words, amplitude modulation is greater for the clean oil. Because error capacitance increases with increasing contaminant concentrations, but decreases with increasing frequency, amplitude modulation decreases as contaminant concentrations increase in a particular oil.

Returning to FIG. 4, the control circuit 18 processes the output from the drive balancing portion 44, as explained above in greater detail, and generates a DC output signal having an amplitude that represents the amplitude modulation of the applied potential, as indicated at step 206. Because amplitude modulation decreases with increasing contaminant concentrations, the amplitude of the output signal will also decrease with increasing contaminant concentrations.

Next, at step 208, the controller 22 processes the output signal to determine the quality of the oil 12. For example, the controller 22 may compare the output signal to a table of predetermined voltage values that correspond with various contaminant concentrations or oil qualities. If the concentration of contaminants exceeds a predetermined level, the controller 22 preferably sends an output signal to the display device 38 as indicated at step 210. The display device 38 may then be used to communicate information regarding oil quality to the operator of the vehicle.

Alternatively, the control circuit 18 may be provided with a controller, such as a micro-controller, for controlling operation of the sensor 11 in order to practice the method according to the invention. The micro-controller may have various computer readable storage media and a microprocessor for executing instructions stored on the computer readable storage media. Alternatively, the controller 22 may be configured to control operation of the sensor 11 in order to practice the method according to the invention.

Because the power source 20, frequency oscillating portion 42, and drive balancing portion 44 preferably cooperate to provide a substantially symmetrically balanced, purely AC potential, the electrodes 17 experience a substantially zero net charge. As a result, migration of polar contaminants and contaminant buildup on the electrodes 17 is substantially reduced. Additionally, by applying the potential during the measurement cycle only, contaminant migration can be further reduced.

Advantageously, the sensor 11 may be configured to minimize undesirable solution current. For example, one or both of the electrodes 17 of the sensor 11 may be coated with an electrically insulating material having a dielectric constant that closely matches the dielectric constant of the oil 12 in a virgin or clean state, in order to inhibit solution current from passing through the oil 12. One example of such an electrically insulating material is TEFLON®. Furthermore, if the potential applied across the electrodes 17 is maintained below the redox potential, undesirable solution current can be substantially eliminated.

Under the method according to the invention, amplitude of the applied potential may also be varied over a range of amplitudes from a first amplitude to a second amplitude less than the first amplitude, while also varying frequency. Because voltage output of an ideal capacitor will increase with increasing frequency, the first and second amplitudes are preferably selected to produce an output signal having a constant amplitude if no error capacitance is present. As a result, if error capacitance is present, the effects of the error capacitance will be more readily apparent. Alternatively, any suitable approach may be utilized to isolate amplitude modulation resulting from the error capacitance. For example, an amplitude correction may be applied to an output signal from the electrodes 17 to compensate for amplitude modulation resulting from factors other than the error capacitance.

Additionally, the control circuit 18 may also be provided with an automatic gain control to adjust maximum voltage peaks of the output from the drive balancing portion 44. As a result, the sensor 11 can be calibrated to produce similar output signals for various virgin or clean oils having varying initial capacitance values. Similarly, the sensor 11 can be calibrated to produce similar output signals for various contaminated oils having similar concentrations of contaminants, but different capacitance values.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for determining quality of lubricating oil using first and second electrodes in contact with the oil, the method comprising:

applying a time-varying potential to the electrodes;

varying frequency of the potential over a range of frequencies from a first frequency to a second frequency;

determining amplitude modulation of the potential over the range of frequencies; and determining the quality of the oil based on the amplitude modulation.

2. The method of claim 1 wherein applying a time-varying potential comprises applying a substantially symmetrically balanced time-varying potential.

3. The method of claim 1 wherein determining amplitude modulation comprises determining amplitude modulation relative to ground.

4. The method of claim 1 wherein determining amplitude modulation comprises determining amplitude modulation between the electrodes.

5. The method of claim 1 further comprising electrically insulating at least one electrode from the oil to inhibit current from passing from the at least one electrode through the oil.

6. The method of claim 5 wherein electrically insulating at least one electrode comprises coating the at least one electrode with teflon.

7. A method for determining quality of lubricating oil, the method comprising:

positioning first and second electrodes in the oil, wherein the electrodes are coated with an electrically insulating material;

applying a symmetrically balanced time-varying potential to the electrodes, the potential having a predetermined amplitude;

sweeping the potential over a range of frequencies from a first frequency to a second frequency;

determining amplitude modulation of the potential over the range of frequencies at the second electrode; and determining the quality of the oil based on the amplitude modulation.

8. A method for determining quality of lubricating oil using electrodes in contact with the oil, the method comprising:

determining error capacitance resulting from electrical double layers that occur proximate the electrodes; and determining the quality of the oil based on the error capacitance.

9. A system for determining quality of lubricating oil, the system comprising:

first and second electrodes adapted to contact the oil; and a microprocessor in communication with the electrodes, the microprocessor including instructions for applying a time-varying potential to the electrodes; instructions for varying frequency of the potential over a range of frequencies from a first frequency to a second frequency greater; instructions for determining amplitude modulation of the potential over the range of frequencies; and instructions for determining the quality of the oil based on the amplitude modulation.

10. A computer readable storage medium having information stored thereon representing instructions executable by a controller to determine quality of lubricating oil using electrodes in contact with the oil, the computer readable storage medium comprising:

instructions for applying a time-varying potential to the electrodes;

instructions for varying frequency of the potential over a range of frequencies from a first frequency to a second frequency;

instructions for determining amplitude modulation of the potential over the range of frequencies; and instructions for determining the quality of the oil based on the amplitude modulation.

11. The computer readable storage medium of claim 10 wherein instructions for applying a time-varying potential comprises instructions for applying a substantially symmetrically balanced time-varying potential.

12. The computer readable storage medium of claim 10 wherein instructions for determining amplitude modulation comprises instructions for determining amplitude modulation relative to ground.

13. The computer readable storage medium of claim 10 wherein instructions for determining amplitude modulation comprises instructions for determining amplitude modulation between the electrodes.

* * * * *